United States Patent [19]

Young et al.

[11] Patent Number: 4,701,555

[45] Date of Patent: Oct. 20, 1987

[54] METHODS FOR REMOVING BIURET FROM UREA BY ADSORPTION

[75] Inventors: Donald C. Young, Fullerton; James A. Green, II, Chino, both of Calif.

[73] Assignee: Union Oil Company of California, Los Angeles, Calif.

[21] Appl. No.: 753,692

[22] Filed: Jul. 10, 1985

[51] Int. Cl.[4] .................. C07C 127/24; C07C 126/08
[52] U.S. Cl. ........................................ 564/38; 564/73
[58] Field of Search ................................... 564/73, 38

[56] References Cited

U.S. PATENT DOCUMENTS

| | | | |
|---|---|---|---|
| 3,150,177 | 9/1964 | Kluge | 564/38 |
| 3,184,508 | 5/1965 | Kaasenbrood | 564/38 |
| 3,185,731 | 5/1965 | Kaasenbrood | 260/555 |
| 3,846,298 | 11/1974 | Plura | 210/33 |
| 3,903,158 | 9/1975 | Fuentes et al. | 260/555 |
| 4,345,099 | 8/1982 | Young et al. | 564/63 |

OTHER PUBLICATIONS

Kucheryavyi et al., Chem. Abs. 68(6): 24698p.
Kirk-Othmer Encyclopedia of Chemical Technology, 2nd edition, vol. 4, pp. 149-151 (1963).
Takahashi & Yoshida, Determination of Biuret in Urea by Ion Exchange Resins, Soil and Plant Food, vol. 3, Jan. 1958, pp. 142-144.
Mithyantha et al., Biuret and Crop Production, Fertilizer News, 1977, pp. 13-18.
Donald C. Young and James A. Green, II, Application Ser. Nos. 567,271 for Methods for Removing Biuret from Urea by Ion Exchange, 567,099 for Ion Exchange Methods for Removing Biuret from Urea, 567,047 for Method for Removing Biuret from Urea, all filed Dec. 30, 1983.
James A. Green II and Donald C. Young, U.S. Application Ser. No. 732,175 filed May 7, 1985, for Manufacture of Biuret.
Donald C. Young and James E. Green, II, U.S. Application Ser. No. 753,693 filed Jul. 10, 1985 for Biuret Purification.
Endo et al., Chem. Abst. 90:143400z.
James A. Green, II, and Donald C. Young, U.S. Application Ser. No. 725,304 filed Apr. 19, 1985 for Methods for Purifying Biuret.

Primary Examiner—Charles F. Warren
Assistant Examiner—Carolyn S. Greason
Attorney, Agent, or Firm—Michael H. Laird; G. Wirzbicki; D. Sandford

[57] ABSTRACT

The biuret content of biuret-containing urea is reduced by contacting a solution or melt of biuret-containing urea with a polar adsorbent under conditions sufficient to remove at least a portion of biuret from the urea. The resulting biuret-containing adsorbent can be regenerated for further use by contact with a polar desorbent under conditions sufficient to desorb at least a portion of the biuret contained on the adsorbent. Optionally, biuret can be recovered by recovering the biuret-containing desorbent, and biuret concentration in the desorbent can be increased by recycling the biuret-containing desorbent into contact with biuret-containing adsorbents, and biuret can be recovered from the desorbent by low temperature crystallization.

32 Claims, No Drawings

METHODS FOR REMOVING BIURET FROM UREA BY ADSORPTION

BACKGROUND OF THE INVENTION

1. Field of the Invention

This invention relates to methods of removing biuret from biuret-containing urea and, in particular, to methods for producing urea of reduced biuret content and for recovering biuret from biuret-containing urea.

2. Description of the Art

Urea is a widely used fertilizer and chemical precursor. Most often it contains some biuret that forms during the urea manufacturing process or when urea is otherwise heated to 130° C. or above. Biuret can interfere with chemical processing and is toxic to many plants. Its phytotoxicity has been thoroughly studied, and it is regulated and monitored by government agencies and industry. For instance, the Indian government prohibits the import of urea containing more than 2 weight percent biuret. The United States agricultural industry generally observes an upper limit of 0.25 weight percent biuret for urea fertilizers classified as "low biuret." This criterion is generally recognized by the citrus and other industries that use urea for foliar fertilization.

Detectable biuret toxicity symptoms have been noted in field tests on lemon and grapefruit in Southern California at biuret levels as low as 0.1 weight percent. Biuret toxicity has also been observed with topically applied urea prills and solutions. Seed germination inhibition and damage to seedlings has been observed in wheat, barley and similar grain crops at levels of 2 weight percent biuret.

Damage to corn has been observed at foliar biuret dosages of 0.2 to 0.5 kilogram per hectare. Thirty percent yield loss was noted in one study at 1.7 kilograms biuret per hectare banded near seeds. Wheat damage has been observed at 0.2 to 0.5 kilogram per hectare foliarly applied, and severe toxicity was observed at 6.0 kilograms per hectare biuret banded in the soil. Fifteen to twenty ppm. soil biuret level has been shown to inhibit barley seed germination while substantial crop damage from foliar application often occurs at 0.4 to 0.6 kilogram biuret per hectare.

Similar effects have been observed in rice, citrus, cotton, avocado, beans, soybeans and potatoes, several of which are particularly sensitive to biuret in foliar fertilizers. In citrus, as little as 0.2 kilograms foliarly applied biuret per hectare causes detectable damage. Avocados are damaged by as little as 50 ppm. biuret in foliar sprays. As little as 3 kilograms per hectare biuret banded in the soil inhibits potato germination and causes citrus damage in light soils. These studies, and a comprehensive review of the literature available on this subject, are presented by Mithyantha, Kulkarni, Tripathi and Agnihothrudu, Fertilizer News, 1977, pp. 13–18.

In view of these results, it is not surprising that the industry has devoted substantial effort to methods of preventing biuret formation in the first instance, and to methods of reducing its concentration once it is formed. Most contemporary commercial urea plants are capable of producing solid and solution urea containing much less biuret than was previously the case. However, essentially all commercial ureas contain at least 0.5 weight percent biuret, and most contain from 1 to 2 weight percent biuret. Biuret content can rise considerably higher if manufacturing conditions are not adequately controlled.

On the other hand, biuret is not without its value. It is widely used in commerce as a precursor for pharmaceuticals, herbicides, and other compounds, as an analytical reagent, and as a ruminant feed supplement. All of these utilities benefit from (if not require) the use of relatively pure biuret.

While biuret can be produced by several chemical methods, it is typically obtained by pyrolyzing urea at a temperature of at least 130° C. and for a period of time sufficient to convert at least a portion of the urea to biuret. An illustrative urea pyrolysis process is discussed by Shipley and Watchorn in British patent No. 1,156,099. As disclosed by Shipley et al., the method produces a mixture of urea, biuret and higher molecular weight urea condensation products such as triuret, cyanuric acid, ammelide, melamine, ammonium cyanurate, methylene diurea, and/or other compounds.

Urea manufactured as solid prills is often treated at temperatures that result in some conversion of urea to biuret and, in many cases, the formation of higher molecular weight compounds as well. While the biuret concentration in prilled ureas is typically low, e.g., 0.5 to 3 weight percent, the amount of biuret contained in such products is substantial due to the large volume of prilled urea manufactured annually. Many of the commercial biuret-containing prilled ureas also contain higher molecular weight urea condensation products such as those mentioned above.

Many of the higher molecular weight condensation products present in some ureas appear to form by the reaction of urea with itself or with previously formed condensation products, or by reactions of, or between, previously formed condensation products. Others, such as methylene diurea, appear to form by the reaction of urea and/or condensation products with additives or other impurities such as formaldehyde which is sometimes employed as a urea anti-caking agent. Regardless of their origin, one or more of such impurities are known to exist in biuret obtained from urea by presently available methods as discussed by Shipley et al., supra, and Kaasenbrood in U.S. Pat. No. 3,185,731.

While urea pyrolysis and prilled urea manufacture afford an ample supply of biuret, the major utilities for biuret benefit from the use of that compound in relatively pure form. Analytical procedures and pharmaceutical and herbicide manufacturing practices involving the use of biuret are most often unacceptably complicated by the presence of higher molecular weight condensation products, and the biuret dosage rate which can be employed in ruminant feed supplements is often limited by the toxicity of such impurities.

Methods presently available for commercially recovering biuret from urea typically involve low temperature crystallization procedures such as those discussed by Shipley et al. and Kaasenbrood, supra, in which the urea and/or biuret are recrystallized several times and separated, and the solid phase is washed to obtain purified urea and/or biuret. While such methods effectively separate biuret from urea, such separation is not complete, and the methods involve expensive, low temperature recrystallization procedures. A substantial amount of biuret generally remains in the urea fraction, and the biuret fraction typically contains minor amounts of urea, even after repeated recrystallization. Furthermore, such procedures do not efficiently separate biuret from urea and cogeneric impurities such as higher molecular weight urea condensation products. Typically, some or all of the higher molecular weight impurities remain in the biuret fraction.

Several authors have disclosed that biuret can be removed from urea by contacting an aqueous biuret-containing solution with the hydroxide ion form of an anion exchanger. For instance, Fuentes et al., U.S. Pat. No. 3,903,158, disclose that impurity biuret can be removed from aqueous urea solutions by ion exchange. Takahashi et al., "Determination of Biuret in Urea by Ion Exchange Resins," Soil and Plant Food, Vol. 3, No. 3, January 1958, pgs. 142-144, disclose that biuret can be separated from aqueous urea solutions and that the biuret retained on the ion exchanger can be eluted to obtain an indication of the biuret concentration in the urea feed.

While such processes are useful for purifying urea, their use for the recovery of biuret from aqueous urea solutions suffers from several disadvantages. Biuret is hydrolyzed and destroyed by the highly basic anion exchangers employed by Fuentes et al. and Takahashi et al. Furthermore, the maximum biuret concentration which could be achieved in an ion exchanger regenerant, such as that employed by Fuentes et al. or Takahashi et al., even in the absence of significant biuret hydrolysis, is at most 0.5 weight percent, and that could occur only in the very initial stages of regeneration. The average biuret concentration in the total regenerant is typically well below 0.1 weight percent. This is because the volume of regenerant typically employed to restore the initial biuret-retaining ability of an ion exchanger, i.e., for regeneration, is so large that the biuret concentration in the total regenerant effluent is much lower than 0.1 weight percent. Almost without exception, it is preferable to completely regenerate ion exchangers to assure the greatest capability for removing the exchanged substance (in this case biuret) in subsequent cycles. Complete regeneration is more readily accomplished by the use of large regenerant volumes. In addition, the use of alkaline regenerants as disclosed by Fuentes et al. destroys biuret as disclosed in our U.S. Pat. No. 4,345,099 for Method of Selectively Removing Biuret from Urea and Compositions for Use Therein, the disclosure of which is incorporated herein by reference in its entirety.

The highest biuret concentrations, if any, obtainable in the exchanger regenerants of Fuentes et al. and Takahashi et al. render those solutions impractical for a variety of reasons. (The strongly alkaline regenerants of Fuentes et al. may not contain any biuret at all unless they are neutralized and/or cooled to prevent biuret hydrolysis.) The solubility of biuret in water at 0° C. is 0.53 weight percent. (Urea, Its Properties and Manufacture, Chao, Chao's Institute, West Covina, Calif., Library of Congress Catalogue Card No. Ai-11524.) Thus, biuret could not be crystallized from solutions of such low biuret concentration unless the solutions were modified to substantially depress their freezing points, and such modification of the solutions might itself prevent biuret crystallization even at lower temperatures. Thus, the commercial use of such solutions would require the shipment of large volumes of water with the attendant cost of such shipment, or evaporation of enough of the water to significantly increase biuret concentration. Obviously, such evaporation adds further expense to the process.

A further disadvantage associated with the prior art methods for separating biuret from urea involves the presence of a significant proportion of higher molecular weight urea condensation products in a substantial portion of biuret-containing ureas. While the prior art crystallization processes could be employed to separate biuret from some of the higher molecular weight urea condensation products, those processes, as mentioned above, require time-consuming, repeated low temperature recrystallization. The expense involved in such methods obviously increases the cost of biuret derived from such sources and limits its application as a result. For instance, ruminant feed supplement manufacturers generally choose to use relatively impure, less expensive biuret at dosage rates which are sufficiently low to avoid the toxic effects of the higher molecular weight impurities. Neither Fuentes et al. nor Takahashi et al. mention the presence of materials other than urea and biuret or the possibility that impurity-free biuret can be recovered from urea solutions which contain higher molecular weight urea condensation products. In fact, Takahashi et al. observe that "usually, urea for agriculture does not contain nitrogen compounds other than biuret." While that is often the case, some urea solutions, and in particular those formed from urea which has been pyrolyzed at temperatures above 130° C. for any significant period of time, contain a significant proportion of urea condensation products of higher molecular weight than biuret, some of which are toxic, and all of which can impair product utility.

The use of strongly basic anion exchangers to remove biuret from urea as disclosed by Fuentes et al. and Takahashi et al., supra, suffers from several further disadvantages. Strongly basic anion exchangers such as Amberlite IRA-400 cost in the range of about $50 to about $150 per cubic foot. The strongly caustic or acidic solutions used to regenerate the exchangers are also relatively expensive. Since, according to the literature, the biuret is relatively strongly held by the anion exchanger (a feature which would be beneficial from the standpoint of assuring adequate removal of biuret from the urea solution), the art suggests that relatively severe regeneration conditions are required to efficiently remove the biuret from the deactivated anion exchanger. Obviously, the cost of anion exchanger regeneration, the cost of constructing, maintaining and operating a system capable of removing biuret from a certain quantity of urea solution, and the expense of the anion exchanger required in the process, all increase as the frequency and/or severity of regeneration increases. Thus, the requirement for frequent and/or more severe regeneration increases regenerant costs and the amount of anion exchanger and the size of the operating facility required to treat a given amount of urea solution.

SUMMARY OF THE INVENTION

It has now been discovered that the biuret content of biuret-containing ureas can be reduced by contacting a solution or melt of the biuret-containing urea with a polar adsorbent. The described contacting can be either batch or continuous, and purified biuret can be recovered from the adsorbent by contacting the adsorbent with a polar desorbent in which biuret is soluble. Optionally, the biuret-containing desorbent can be recycled into contact with the same or other biuret-containing adsorbents to increase the biuret concentration of the desorbent, and biuret can be recovered from the concentrated desorbent.

The methods of this invention overcome many of the disadvantages associated with prior art methods of reducing the biuret content of urea and/or of producing biuret. They eliminate the need for expensive, basic anion exchangers and complicated regeneration procedures attendant to the use of such exchangers. In doing so, they eliminate the consumption of chemicals such as regenerants which are consumed in the regeneration of ion exchangers and in the hydrolysis of biuret. They eliminate the potential loss of biuret by hydrolysis on strongly basic anion exchangers or by the caustic regenerants used to regenerate such exchangers, at least according to the art. Thus, these methods provide for the recovery of purified, i.e., biuret-free urea, as well as the recovery of biuret. They further provide for the inexpensive and efficient production of concentrated biuret solutions of sufficiently high biuret concentration to enable biuret recovery by low temperature crystallization, solvent extraction or other procedures.

One embodiment of this invention further provides for extending the useful life of the adsorbent by excluding strongly adsorbed compounds such as carbonates and sulfates from the urea feed and/or desorbent solutions and/or by regenerating the adsorbent with solutions of polar salts, acids, or bases.

DETAILED DESCRIPTION OF THE INVENTION

The invention provides methods for reducing the biuret content of biuret-containing ureas which involve contacting a solution or melt of biuret-containing urea with a polar adsorbent under conditions sufficient to retain at least a portion of the biuret on the adsorbent. Urea of reduced biuret content can be recovered from the adsorbent, and, optionally, biuret can be recovered from the adsorbent by contacting the biuret-containing adsorbent with a polar desorbent in which biuret is soluble under the contacting conditions. Furthermore, the concentration of biuret in the biuret-containing desorbent can be increased by recycling the desorbent into contact with the same or other biuret-containing adsorbents under conditions sufficient to increase the biuret content of the desorbent, and the adsorbent can be regenerated, as required, for adsorption of biuret from additional urea solutions or melts by contact with water or an aqueous solution of salt, base or acid sufficient to displace biuret and other adsorbed materials.

The described methods can be employed to reduce the biuret content of any biuret-containing urea solution or melt. Urea melts are usually classified as compositions which contain less than about 5, generally less than 2, and typically less than about 1 weight percent water or other solvent, the remainder being urea, biuret, and/or higher molecular weight urea condensation products. Such compositions are contacted with the adsorbents in accordance with this invention at temperatures in excess of the melting point of the urea-biuret composition. Biuret-containing solutions include solutions of urea and biuret in water or polar organic solvents in which both urea and biuret are soluble such as dimethylsulfoxide, methanol, amylalcohol, quinoline, dimethylether, glycerol, pyridines, ethyl acetate, etc.

Biuret-containing urea solutions useful in this invention include, without limitation, solutions recovered from any stage of the urea manufacturing process, solutions formed by dissolving urea such as prilled or pelleted urea in water or polar organic solvents, and solutions formed by dissolving urea which has been heat-treated to increase its biuret content. These solutions, especially those which have been heat-treated, may also contain higher molecular weight urea condensation products, such as triuret, cyanuric acid, ammonium cyanurate, cyclic polyamides such as melamine and ammelide, and others. Biuret-containing urea solutions from which a portion of the biuret and/or urea have been separated by crystallization or otherwise as discussed, for instance, in British patent No. 1,156,099 or U.S. Pat. No. 3,185,731, supra, may also be employed in these methods. Such solutions may also contain higher molecular weight urea condensation products. The disclosures of British patent No. 1,156,099 and U.S. Pat. No. 3,185,731 are incorporated herein by reference in their entireties.

Many commercially available urea solids and solutions contain about 0.5 to about 3 weight percent biuret based on urea. Such ureas may also contain higher molecular weight urea condensation products. The higher molecular weight impurities typically constitute at least about 5, generally at least about 10, and most often about 5 to about 50 weight percent of the composition based on biuret. Triuret, when present, usually accounts for approximately one-half of the impurity content of impure prilled ureas. Ureas which have been intentionally pyrolyzed, i.e., heated to form biuret, typically contain substantially higher proportions of biuret and higher molecular weight urea condensation products.

Pyrolysis is usually effected by treatment at a temperature of at least about 135° C., generally about 135° to about 180° C., for a period of time sufficient to convert at least a portion of the urea to biuret. Contact times of at least about 2 minutes are usually employed, although significant urea conversion usually requires treatment for about 5 minutes to about 5 hours. The rate of urea conversion increases with temperature; thus, the contact time required to achieve a certain degree of urea pyrolysis decreases as treatment temperature is increased.

While all of the urea can be pyrolyzed to biuret and higher molecular weight urea condensation products, higher conversions require the use of higher temperatures and/or longer contact times which result in higher impurity/biuret ratios and the loss of biuret product. Biuret loss under severe pyrolysis conditions is due, at least in part, to the pyrolysis of biuret to higher molecular weight compounds. Thus, the urea is typically only partially pyrolyzed under conditions sufficient to yield at least about 5 weight percent, generally about 10 to about 50 weight percent biuret based on urea. The higher biuret concentrations are usually associated with higher impurity/biuret ratios due to the more severe pyrolysis required to achieve such biuret levels. Further explanation of the relationship of pyrolysis time and temperature and of impurity concentration is given in "Urea, Its Properties and Manufacture, George C. Tsei-Yu-Chao, 1967, Library of Congress Catalog Card number Ai-11254, published by Chao's Institute, West Covina, Calif. particularly on pages 119–123, the disclosure of which is incorporated herein by reference.

Regardless of their source or the method of their manufacture, the useful biuret-containing urea feed solutions typically contain about 1 to about 80 weight percent, generally about 2 to about 70 weight percent solute, including urea and biuret in the presence or absence of higher molecular weight urea condensation products. Maximum solution concentration is usually determined by solution temperature which can range from 10° C. to about 100° C. However, at temperatures above 70° C. urea decomposition by hydrolysis in aqueous solutions becomes more rapid. Accordingly, aqueous solutions which contain substantial urea are preferably maintained at about 70° C. or less.

Urea has a solubility of approximately 80 weight percent in water at 70° C. and biuret will dissolve in water to a level of approximately 20 weight percent at the same temperature. However, biuret is more soluble in both aqueous and non-aqueous urea solutions. Thus, higher biuret concentrations can be achieved in the presence of substantial amounts of dissolved urea.

While the aqueous biuret-containing urea solutions can be employed as prepared, they usually contain sufficient ammonia to produce a relatively basic aqueous solution. Although this condition can be tolerated, pH levels of about 12 and above promote urea and biuret hydrolysis, particularly in aqueous systems, and are preferably avoided. Accordingly, aqueous feed solutions will usually be relatively non-alkaline and will generally have a pH below 12, usually about 10 or less, preferably about 6 or less, and most preferably about 3 to about 6. Alkaline aqueous solutions can be neutralized and/or buffered to obtain the desired pH by adding any suitable organic or inorganic acid such as sulfuric, hydrochloric, nitric, acetic, etc., or buffering agents such as ammonium polyphosphate. Relatively acidic solutions are particularly preferred for use at higher temperatures and/or longer contact times.

The useful adsorbents include all polar adsorbents including natural and synthetic, amorphous and crystalline, organic and inorganic, acidic, neutral and basic adsorbent materials. They are distinguished from ion exchangers such as those discussed by Fuentes et al. and Takahashi et al., supra, in that they typically have ion exchange capacities of less than about 0.1, generally less than 0.05 milliequivalents of exchange capacity per ml. (meq./ml.) of adsorbent. Ion exchangers, including ion exchange resins, aluminosilicates and other inorganic oxides typically have exchange capacities of 0.13 to 2.0 meq./ml. The term "adsorbents" is used herein in its conventional sense to connote solid materials which retain one or more components of gases or solutions predominantly, if not exclusively, by mutual physical-chemical attraction rather than by the literal exchange of ions which is the predominant mechanism of ion exchange processes. Typically, the adsorbent's biuret adsorption capacity is at least about twice its ion exchange capacity (if any).

Illustrative inorganic adsorbents include natural and synthetic, amorphous and crystalline oxides, such as silica, oxides of metals such as beryllium, magnesium, calcium, boron, aluminum, gallium, etc., e.g., alumina, magnesia, beryllia, borax, magnesium silicates, magnesium hydrogen silicates, calcium silicates, aluminosilicates and mixtures or coprecipitates of such oxides. In addition, suitable adsorbents can be obtained by impregnating a porous substrate with one or more of such polar adsorbents, and the polar adsorbent or impregnated adsorbent, as the case may be, can be acid or caustic treated or calcined to modify its physical or chemical properties. When calcination is employed, however, relatively low temperatures are presently preferred since extreme temperatures, e.g. 800° C. and above, can dehydroxylate adsorbents and convert them to relatively non-polar materials. Examples of suitable polar inorganic adsorbents include silica gel, boehmite alumina, Florisil, Magnesol, Silicalite, silica-beryllia cogels, clays such as montmorillonite, halloysite, kaolinite, diatomaceous earth, celite, kiesselguhr, organoclays such as derivatives of montmorillonite which have been exchanged with quaternary ammonium ions to form bentones, etc.

Illustrative organic adsorbents include oxidized carbons, natural and synthetic polymers which contain pendant polar groups such as hydroxyl, carboxyl, sulfate, sulfite, amino, amido, thiol, thio, oxy, phosphate, phosphite, etc. including homo-, co-, graft, and substituted (chemically modified) polymers. Specific organic adsorbents include charcoal which has been oxidized at temperature of less than about 400° C., untreated or acid and/or caustic-treated cellulosic matter, e.g., cotton, paper, sawdust, dehydrated plant matter, and other cellulosic material, polyacrylates such as polymers of acrylic acid, ethylhexylacrylate, hydroxyethylacrylate, methacrylic acid, ethyl methacrylate, and the like, phenolics such as phenolformaldehyde polymers, polyethylene thiols, polycaprolactam, etc. Particularly practical organic adsorbents include cellulose and the acrylate polymers due, primarily, to their availability and relatively low cost. Suitable adsorbents are commercially available from several manufacturers such as Bio-Rad Laboratories of Richmond, Calif. which markets a silica adsorbent as Bio-Sil A ®, neutral, basic and acidic alumina as grades AG-7, AG-10, and AG-4, respectively, and a polar acrylic ester adsorbent as Bio-Beads SM-7 ®.

In addition to the above noted chemical characteristics of suitable adsorbents, they should contain sufficient surface area to present adequate surface for the adsorption of biuret from the urea melts or solutions. Typically, such adsorbents will have surface areas of at least about 10, and generally at least about 50 square meters per gram.

All of the process steps, including the extraction of biuret from the urea feed and the removal of biuret from the resulting biuret-containing adsorbent, can be performed either by batch contacting or by continuous plug flow contacting in which the feed, desorbent and/or regenerant solutions are passed through the adsorbent retained in a relatively fixed bed. Plug flow systems can be operated either downflow or upflow, although downflow systems are generally preferred.

Each increment of the biuret-containing feed is usually contacted with the adsorbent for at least about 30 seconds, preferably at least about one minute, most preferably at least about 5 minutes, and generally about one minute to about one hour. Contact times of about 5 to about 30 minutes are usually adequate to effect the desired degree of biuret removal. Such contact times correspond to flow rates of about 2 bed volumes per minute or less, usually about 1 bed volume per minute or less, preferably about 0.2 bed volumes per minute or less, and most preferably about 0.02 to about 1 bed volume per minute.

Contact of the adsorbent with the biuret-containing feed is usually, although not necessarily, continued until the capacity of the adsorbent is depleted. Depletion of adsorbent capacity is indicated in the preferred, continuous, fixed bed systems by biuret breakthrough, which occurs when a detectable quantity of biuret is present in the product recovered from the adsorbent. However, the biuret sorption step can be continued past the point of biuret breakthrough if desired.

The biuret-containing urea can be contacted with the adsorbent at any temperature above the freezing point and below the upper temperature limit (e.g., boiling point, decomposition temperature, etc.) of the solution or melt. Typically, the feed will be contacted with the exchanger at a temperature of about 0° to about 100° C., generally about 25° to about 70° C. and preferably about 30° to 70° C. While higher temperatures can be employed, urea decomposition rate (to $CO_2$ and ammonia) increases rapidly at temperatures above 70° C., especially in water, and such temperatures are preferably avoided. Higher temperatures increase solubility and biuret sorption rate and thereby reduce the time required to sorb a given quantity of biuret. They also markedly increase urea and biuret hydrolysis rates in alkaline aqueous systems. Therefore, it is preferable to acidify aqueous feed solutions at least to about neutrality and preferably to a pH below 7 when higher contacting temperatures are employed.

After the biuret sorption step, excess feed is removed from the adsorbent, and the biuret-containing adsorbent can be contacted with a desorbent under conditions sufficient to form a biuret-containing desorbent substantially free of higher molecular weight urea condensation products (when such products are present in the feed). The desorbent can be contacted with the adsorbent by either batch or column operations as described above with regard to the biuret sorption step.

It is sometimes desirable, although not essential, to backwash the adsorbent to remove foreign matter, to flush remaining feed from the adsorbent and/or to "reclassify" the bed of adsorbent matter. Backwashing is usually effected by passing water or other solvent rapidly upwardly through the bed to expand the bed by, e.g., 50 percent. However, substantial backwashing of the biuret-containing adsorbent at this point in the operation is not preferred since even neutral water is capable of removing biuret from the adsorbent. Thus, biuret recovery can be maximized, when that is an objective, by deferring substantial backwashing until the biuret recovery step is completed as described hereinafter. However, the adsorbent can be washed with a minor amount of water, e.g. one bed volume or less, and/or can be blown free of residual feed with a pressurized gas such as air, nitrogen, etc., to reduce or prevent contamination of the biuret product with the feed and other impurities.

The useful desorbents are polar, organic or inorganic, acidic, neutral or alkaline materials in which biuret is soluble under contacting conditions. Although desorbents which are less polar than biuret can be employed for this purpose, preferred desorbents are more polar than biuret since they more readily displace biuret from the adsorbent. Illustrative desorbents include water, acidic or basic aqueous media such as aqueous sulfuric acid, hydrochloric acid, nitric acid, sodium hydroxide, calcium hydroxide, ammonium hydroxide, organic desorbents such as aldehydes including formaldehyde, propionaldehyde, ketones such as methylethylketone, alcohols such as isopropanol, organic acids such as acetic, butyric, propionic, etc., amines, amides, thiols, and other polar compounds and combinations of such compounds. Aqueous neutral, basic or acidic desorbents are presently preferred for economy and due to the high solubility of biuret in such desorbents. Substantially non-alkaline desorbents are presently preferred for recovering biuret since alkaline materials promote biuret hydrolysis. Thus, deionized water and distilled water are presently preferred, and these can be acidified if desired. The most preferred aqueous desorbents usually have a pH of about 7 or less, preferably below about 6, and generally within the range of about 1 to about 7. Any organic or inorganic acid can be employed to effect the desired degree of acidification.

The biuret-containing adsorbent is contacted with a sufficient volume of desorbent for a sufficient period of time to remove a substantial proportion of the biuret from the adsorbent. Typically, at least one volume of desorbent will be employed per volume of adsorbent, although much higher desorbent volumes can be used. Thus, desorbent volume will usually range from about 1 to about 100 volumes per volume of adsorbent, although most operations will involve about 1 to about 10 volumes of desorbent per volume of adsorbent.

In at least one respect, desorbent volume is inversely proportional to biuret concentration in the extract since biuret concentration is a function of total desorbent volume and the quantity of biuret removed from one or more adsorbents by that volume of desorbent. The quantity of biuret removed is a direct function of the biuret content of the adsorbent and the quantity of adsorbent contacted with a given volume of desorbent. Thus, biuret concentration can be increased by either decreasing desorbent volume and/or increasing the quantity of biuret-containing adsorbent contacted with a fixed volume of desorbent. As a general rule, each volume of desorbent will be contacted with at least about 0.1, typically at least about 0.2 and preferably at least about 0.5 equivalent volume of adsorbent which is initially saturated with biuret. Higher effective desorbent/adsorbent volume ratios can be achieved by recycling a given volume of desorbent more than once and by reducing the total quantity of desorbent employed to regenerate a given quantity of adsorbent. In the latter instance, the volume of desorbent passed over the adsorbent during a given desorption cycle will typically be about 20 volumes or less, preferably about 18 volumes or less per volume of adsorbent.

Shorter contact times are required to achieve the same degree of biuret removal at higher temperatures due to increased biuret solubility and high desorption rates. Thus, contact time can be varied depending on the temperature employed. Typically, contact times for the desorption step will be at least about 10 minutes to about 5 hours. Such contact times, in fixed bed systems, correspond to desorbent flow rates of less than about 10, preferably less than about 5 volumes of extract per volume of adsorbent per hour (V/V/hr.).

The temperature of aqueous desorbents should be sufficiently low to prevent substantial biuret hydrolysis, particularly when alkaline desorbents are employed. Thus, temperatures are generally below 40° C. and preferably below 30° C. when basic aqueous desorbents are used. Biuret hydrolysis in alkaline systems is relatively slow at 24° C.

Organic (anhydrous) and neutral or acidic aqueous desorbents can be employed at higher temperatures without significant biuret hydrolysis, and higher temperatures are presently preferred due to the higher solubility of biuret at such temperatures. For instance, biuret solubility in pure water is 0.53 weight percent at 0° C., 2 percent at 25° C., 7 percent at 50° C., 20 percent at 75° C., and almost 48 percent at 100° C. Elevated temperatures also increase biuret desorption rate. Accordingly, anhydrous or neutral or acidic aqueous desorbents and elevated temperatures of at least about 25° C., generally about 25° to about 100° C., and preferably about 30° to about 100° C. are presently employed.

Desorbent-adsorbent contacting can be by either batch or co-current or countercurrent fixed bed procedures or combinations of these. Furthermore, single or multiple contacts with the same or different desorbent can be employed in both batch and fixed bed systems. After a fresh quantity of desorbent has been contacted with a biuret-containing adsorbent, the resulting biuret-containing desorbent can be recycled into contact either with the same adsorbent or with another biuret-containing adsorbent to increase the biuret concentration in the desorbent. Also, the first portion of extract (a fraction of an adsorbent volume up to several volumes) recovered from the adsorbent, which typically has a higher biuret content than subsequent portions of extract, can be recovered as product and/or processed by crystallization, evaporation, etc., and subsequent portions, typically of lower biuret content, can be recycled.

The desorbent can be recycled up to 100 times or more depending on the biuret concentration desired, contact time between each volume of desorbent during each cycle, temperature, and the quantity of biuret on each adsorbent contacted. Usually, however, when the desorbent is recycled, the desorbent, or a portion thereof, will be recycled 1 to about 20 times unless biuret is recovered from the extract. Biuret-containing desorbent recovered after contact with a biuret-containing adsorbent is typically recycled for a total of at least about three cycles, preferably at least about five, and most preferably at least about ten cycles. Biuret concentration can be increased each time the desorbent is recycled until the solubility limit is reached at operating temperature. A fixed volume of desorbent can be recycled indefinitely provided that biuret is recovered from the desorbent (extract) by crystallization or otherwise.

Product extract obtained when biuret recovery is desired will typically contain more than 0.5 weight percent, generally at least about 1 weight percent, and often about 2 to about 50 weight percent biuret. Biuret concentrations of at least about 4 weight percent, particularly at least about 10 weight percent, are preferred for the production of more concentrated solutions, e.g. by evaporation, or for the production of solid biuret by crystallization or otherwise. The higher biuret concentrations can be achieved by the use of longer contact times, lower volumes of desorbent per volume of adsorbent, higher adsorbent biuret loadings, higher contacting temperatures, higher recycle ratios, or combinations of two or more of these procedures.

Following recovery of the biuret-containing extract from the adsorbent, the adsorbent can be employed to remove biuret from additional quantities of the impure biuret-containing feed mixture with or without further regeneration. Occasionally, however, adsorbent activity may become diminished due to the adsorption of strongly adsorbed compounds such as alkali and alkaline earth metal, carbonates and sulfates, which may not be completely desorbed during the desorption step. Adsorbent capacity can also be depleted by adsorption of impurities from the biuret-containing feed which are not desorbed during the desorption step. For these reasons, it is preferable, when adsorbent activity declines, to further regenerate the adsorbent with a strongly polar regenerant such as aqueous, caustic, and/or acid solutions. Regeneration with strong caustic, e.g. 2 to about 8 weight percent sodium hydroxide solution, or acids such as 2 weight percent aqueous hydrochloric and/or sulfuric acids, is usually sufficient to restore most if not all of the adsorbent activity. Adsorbent-regenerant contacting can be carried out by batch or continuous operations as described above with regard to the biuret adsorption step. Typically, such regeneration involves contacting the adsorbent with at least one volume of regenerant per volume of adsorbent for at least about 1 minute, typically about 1 to about 20 minutes, sufficient to displace adsorbed compounds and restore the active polarity of the adsorbent. In the alternative, the inorganic adsorbents and carbon can be reactivated by washing them free of readily elutable materials (caustic and/or acid washing can also be employed in this step) followed by heating in an oxidizing atmosphere such as air to a temperature sufficient to restore the adsorbent's activity. Activation temperatures involved in such procedures are typically at least about 200° C., often at least about 400° C., and should not exceed the deactivation or sintering temperatures of the adsorbent and, therefore, are generally kept below 800° C.

Extracts prepared from urea solutions or melts containing higher molecular weight urea condensation products in accordance with one embodiment of this invention contain substantially lower proportions of the higher molecular weight urea condensation products present in the feed. Typically, the proportion of higher molecular weight impurities present in the extract will be less than one half, preferably less than one tenth, the concentration of those impurities in the feed solution based on biuret. Thus, biuret of greater than 95 percent purity can be obtained by these methods. When care is taken to avoid contamination of the extract with the residual feed on the adsorbent, biuret purity of at least about 99 percent and even 99.9 percent plus can be achieved.

The recovered biuret-containing extract can be employed as is as a herbicide, chemical precursor, animal feed supplement, or for other utilities. Alternatively, a proportion or all of the solvent (desorbent) in the extract can be evaporated to obtain either crystalline biuret or a concentrated biuret solution. When elevated temperature evaporation is employed with aqueous extracts, care should be taken to assure that the extract is approximately pH neutral or acidic prior to exposure to elevated temperatures to avoid biuret loss.

In a particularly preferred embodiment, the biuret concentration in the extract is increased either by recycling or otherwise as described above or by evaporation to obtain a biuret concentration of at least about 4 weight percent, preferably at least about 10 weight percent, after which the concentrated solution is chilled to a temperature, e.g. about 0° C., sufficient to crystallize biuret from the solution. The crystalline biuret can be recovered by any suitable solid-liquid separation means such as filtration, decanting, etc.

The invention is further described by the following examples which are illustrative of specific modes of practicing the invention and are not intended as limiting the scope of the invention as defined by the appended claims.

EXAMPLE 1

30 grams of cotton is thoroughly washed with deionized water on a filter funnel, after which 50 grams of 10 weight percent urea solution containing 1.38 weight percent biuret based on urea is allowed to percolate through the cotton adsorbent while on the filter funnel at a rate of one drop per second. Three 15 ml. samples are taken consecutively and are analyzed for urea and biuret by liquid chromatography. The results, summarized in Table 1, demonstrate that the biuret concentration of the treated urea solution has been reduced at least 98 percent.

TABLE 1

|  | Urea (U) g/l | Biuret (B)[a] g/l | B/U wt. ratio[a] × $10^2$ |
|---|---|---|---|
| Urea Feed | 102.5 | 1.414 | 1.380 |
| Fraction 1 | 24.9 | 0.007 | 0.03 |
| Fraction 2 | 32.4 | 0.008 | 0.02 |
| Fraction 3 | 32.8 | 0.00 | 0 |

[a] The results for fractions 1, 2, and 3 are equivalent within the range of analytical error.

EXAMPLE 2

30 grams of cotton is placed in a 250 ml. Erlenmeyer flask and treated with 200 g. of 4 weight percent sodium hydroxide solution for three hours. The treated cotton is then placed in a filter funnel and washed thoroughly with deionized water. 50 grams of 10 weight percent urea solution containing 1.38 weight percent biuret based on urea is then allowed to percolate through the cotton while on the filter funnel at a rate of one drop per second. Three 15 ml. samples of the treated urea solution are taken consecutively and are analyzed by liquid chromatography for urea and biuret. The results are summarized in Table 2.

TABLE 2

|  | Urea (U) g/l | Biuret (B) g/l | B/U wt. ratio × $10^2$ |
|---|---|---|---|
| Urea Feed | 102.5 | 1.414 | 1.380 |
| Fraction 1 | 32.3 | 0.044 | 0.136[a] |
| Fraction 2 | 38.2 | 0.015 | 0.04 |
| Fraction 3 | 35.8 | 0.016 | 0.04 |

[a] High value of first fraction is due to channeling of feed through adsorbent bed.

Comparison of the biuret concentration of the recovered desorbent to the biuret concentration in the urea feed solution demonstrates that this treatment reduced the biuret content of the urea solution by approximately 98 percent.

EXAMPLE 3

Purified biuret can be recovered from an aqueous solution containing 40 weight percent urea, 3 weight percent biuret based on urea, and 10 weight percent higher molecular weight urea condensation product based on biuret (including triuret and melamine), by passing the solution downwardly over a packed bed of silica gel at a rate of 0.3 bed volumes per minute and a temperature of 40° C. to remove a substantial portion of the biuret from the feed solution and retain the removed biuret on the silica adsorbent. Urea feed solution flow can then be discontinued, residual urea feed solution can be removed from the adsorbent, and biuret can be recovered from the adsorbent by contact with 20 bed volumes of deionized water desorbent passed downwardly over the adsorbent bed at a rate of 0.3 bed volumes per minute. The described biuret adsorption and desorption steps can be repeated for five consecutive cycles by recycling the biuret-containing desorbent recovered from each preceding cycle as the desorbent in each succeeding cycle to obtain an extract which is more concentrated in biuret and which contains a lower proportion of higher molecular weight urea condensation products relative to biuret than is present in the urea feed solution.

While particular embodiments of this invention have been described, it will be understood, of course, that the invention is not limited thereto since many obvious modifications can be made, and it is intended to include in this invention any such modifications as will fall within the spirit and scope of the appended claims.

We claim:

1. A method for reducing the biuret content of biuret-containing urea which comprises contacting a solution or melt of said biuret-containing urea with a polar adsorbent.

2. The method defined in claim 1 wherein the resulting urea of reduced biuret content is separated from said adsorbent.

3. The method defined in claim 1 wherein said adsorbent comprises a member selected from the group consisting of silica, alumina, magnesia, beryllia and combinations thereof.

4. The method defined in claim 1 wherein said adsorbent comprises a member selected from the group consisting of natural and synthetic organic adsorbents which comprise a polar group selected from the group consisting of hydroxide, carbonyl, carboxyl, sulfate, phosphate, amino, amido, and combinations thereof.

5. The method defined in claim 4 wherein said adsorbent comprises a member selected from the group consisting of cellulose and acrylate polymers and combinations thereof.

6. The method defined in claim 2 wherein said biuret is removed from said adsorbent by contacting said adsorbent with a polar desorbent in which biuret is soluble.

7. The method defined in claim 6 wherein said desorbent comprises water.

8. The method defined in claim 6 wherein the resulting desorbent containing biuret is recycled into contact with a biuret-containing adsorbent under conditions sufficient to increase the biuret concentration of said desorbent.

9. The method defined in claim 6 wherein said desorbent is contacted with said biuret-containing adsorbent under conditions sufficient to obtain a desorbent containing at least about 0.5 weight percent biuret.

10. The method defined in claim 9 which comprises the step of recycling the biuret-containing desorbent recovered from said adsorbent into contact with a biuret-containing adsorbent under conditions sufficient to increase the biuret concentration of said desorbent.

11. The method defined in claim 10 wherein said desorbent is substantially non-alkaline.

12. The method defined in claim 10 wherein said biuret-containing desorbent is recycled into contact with a biuret-containing adsorbent under conditions sufficient to obtain a desorbent having a biuret concentration of at least about 1 weight percent.

13. The method defined in claim 6 wherein said desorbent comprises an alkaline aqueous solution having a pH of at least about 12, and said biuret-containing desorbent recovered from said adsorbent is recycled into contact with at least 1 biuret-containing adsorbent.

14. The method defined in claim 13 wherein said desorbent comprises a member selected from the group consisting of sodium hydroxide, potassium hydroxide, ammonium hydroxide and combinations thereof.

15. The method defined in claim 6 wherein said desorbent is substantially non-alkaline.

16. The method defined in claim 1 wherein said biuret-containing urea is contacted with said adsorbent as an aqueous solution.

17. The method defined in claim 1 wherein said biuret-containing urea is contacted with said adsorbent as a biuret-containing urea melt at a temperature above the melting point of said biuret-containing urea.

18. A method for recovering biuret from biuret-containing urea which comprises contacting a melt or solution of said biuet-containing area with a polar absorbent for a period of about 1 minute to about 1 hour under conditions sufficient to adsorb at least a portion of the biuret from said urea onto said adsorbent, separating the resulting urea of reduced biuret content from said adsorbent, contacting the resulting biuet-containing adsorbent with a polar desorbent in which said biuret is soluble, and separating the resulting biuret-containing desorbent from said adsorbent.

19. The method defined in claim 18 wherein said desorbent is an aqueous desorbent having a pH of about 10 or less.

20. A method for recovering biuret from biuret-containing urea which comprises contacting a solution or melt of said biuret-containing urea with a polar adsorbent retained in a fixed bed by passing said biuret-containing urea through said fixed adsorbent bed at a flow rate corresponding top about 0.2 to about 1 bed volume per minute.

21. The method defined in claim 20 wherein said desorbent comprises water.

22. The method defined in claim 20 wherein said desorbent comprises a substantially non-alkaline aqueous medium having a pH below about 10.

23. The method defined in claim 20 wherein said desorbent is contacted with a biuret-containing adsorbent for a total of at least three cycles and under conditions sufficient to increase the biuret content of said desorbent to at least about 1 weight percent.

24. The method defined in claim 20 wherein said desorbent is contacted with a biuret-containing adsorbent for at least three cycles and under conditions sufficient to increase the biuret concentration of said desorbent to at least about 4 weight percent, and, during at least one of said cycles, said desorbent is contacted with a biuret-containing adsorbent at a temperature of at least about 30° C.

25. The method defined in claim 21 wherein said desorbent is contacted with said biuret-containing adsorbent at a pH of about 6 or less.

26. The method defined in claim 24 wherein said desorbent is contacted with a biuret-containing adsorbent during at least one of said cycles at a temperature of at least about 50° C.

27. The method defined in claim 20 which further comprises the step of cooling said biuret-containing desorbent to a temperature sufficient to crystallize at least a portion of said biuret from said desorbent.

28. The method defined in claim 20 wherein said biuret-containing urea comprises at least about 5 weight percent biuret.

29. The method defined in claim 20 wherein said biuret-containing urea is contacted with said adsorbent as an aqueous solution of said biuret-containing urea, said aqueous solution comprises at least about 10 weight percent urea and at least 10 weight percent biuret based on said urea, and said solution is prepared, at least in part, by heating urea to a temperature of at least about 135° C. for a period of time sufficient to convert at least a portion of said urea to biuret.

30. The method defined in claim 20 wherein said biuret-containing desorbent is recycled into contact with one or more biuret-containing adsorbents for a number of cycles sufficient to increase the biuret content of said desorbent to a level above the biuret solubility limit in said desorbent at 0° C., and the resulting biuret-containing desorbent is cooled to a temperature sufficient to crystallize at least a portion of said biuret from said desorbent.

31. The method defined in claim 20 wherein said desorbent is contacted with said adsorbent by passing said desorbent through said bed, and said adsorbent has an ion exchange capacity no greater than about 0.1 meq./ml.

32. A method for reducing the biuret content of biuret-containing urea which comprises contacting a melt or solution of said urea with (A) a member selected from the group consisting of natural and synthetic oxides of silicon, aluminum, beryllium, magnesium, calcium, boron, gallium and combinations thereof, or (B) a member selected from the group consisting of oxidized carbon and natural and synthetic polymers containing pendant polar groups selected from hydroxyl, carboxyl, sulfate, sulfite, amino, amido, thiol, thio, oxy, phosphate, phosphite, and combinations thereof, under conditions sufficient to adsorbe at least a portion of said biuret from said urea.

* * * * *